US005741802A

United States Patent [19]
Kem et al.

[11] Patent Number: 5,741,802
[45] Date of Patent: Apr. 21, 1998

[54] ANABASEINE DERIVATIVES USEFUL IN THE TREATMENT OF DEGENERATIVE DISEASES OF THE NERVOUS SYSTEM

[75] Inventors: William R. Kem; John A. Zoltewicz; Edwin M. Meyer; Katalin Prokai-Tatrai, all of Gainesville, Fla.

[73] Assignee: University of Florida, Gainesville, Fla.

[21] Appl. No.: 392,763

[22] PCT Filed: Aug. 31, 1993

[86] PCT No.: PCT/US93/08192

§ 371 Date: Jan. 5, 1996

§ 102(e) Date: Jan. 5, 1996

[87] PCT Pub. No.: WO94/05288

PCT Pub. Date: Mar. 17, 1994

Related U.S. Application Data

[63] Continuation-in-part of Ser. No. 938,427, Aug. 31, 1992, abandoned.

[51] Int. Cl.$^6$ .......................... A61K 31/44; C07D 211/68
[52] U.S. Cl. .......................... 514/334; 514/318; 546/193; 546/257
[58] Field of Search .................... 514/318, 334; 546/193, 257

[56] References Cited

U.S. PATENT DOCUMENTS

| | | | |
|---|---|---|---|
| 3,247,213 | 4/1966 | Buchel et al. | 546/193 |
| 3,265,573 | 8/1966 | Goldberg | 514/223.2 |
| 3,275,625 | 9/1966 | Muller et al. | 544/13 |
| 3,426,130 | 2/1969 | Riffkin et al. | 514/223.2 |
| 4,155,909 | 5/1979 | Sanders et al. | 546/193 |
| 4,195,645 | 4/1980 | Bradley et al. | 131/337 |
| 4,965,074 | 10/1990 | Lesson et al. | 424/449 |
| 5,602,257 | 2/1997 | Zoltewicz | 546/193 |

FOREIGN PATENT DOCUMENTS

| | | |
|---|---|---|
| WO 92/15306 | 9/1992 | WIPO . |
| WO 94/05288 | 3/1994 | WIPO . |
| Wo 95/15759 | 6/1995 | WIPO . |

OTHER PUBLICATIONS

Wiley et al., "Synthesis of 4-(Methylnitrosamino)-1-(3-Pyridil)-1-Butanone, 4-(carbethoxynitrosamino)-1-(3-Pyridyl)-1-Butanone, and N'-Nitrosonornicotine Labelled With Tritium in the Pyridine Ring," Journal of Labelled Compounds and Radiohparmaceuticals, XXV(7):707-716.

Zoltewicz et al., "Hydrolysis of Cholinergic Anabaiseine and Anabaseine-N-Me," *Bioorganic Chem.*, 18:403, 1990.

Zoltewicz et al., "Quantitative Determination of the Ring-Chain Hydrolysis Equilibrium Constant for Anabaseine and Related Tobacco Alkaloids," *Journal of Organic Chemistry*, 64(18):4462-4468, 1989.

Parcell et al., "The preparation of Tetrahydro pyridines from Enamies and Imines," *J. of Organic Chemistry*, 28:3469, 1963.

Pathak et al., "Synthesis of [4-$^2$H$_2$]-, (4R)[4-$^2$H$_1$]-and (4S)[4-$^2$H$_1$] -4-(Methylnitrosamino)-1-(3'-Pyridyl-1-Butanone, C-4 Deuteriated Isotopomers of the Procarcinogen NNK," *Tetrahedron* 46(5):1733-1744, 1990.

Patneau et al., "Hippocampal Neurons Exhibit Cyclothiazide-sensitive Rapidly Desensitizing Responses to Kainate," *The Journal of Neuroscience*, 13(8):3496-3509, 1993.

Seeman et al., "Steric and Conformational Effects in Nicotine Chemistry," *J. Org. Chem.*, 46:3040-3048, 1981.

Topliss et al., "Antihypertensive Agents. I. Non-diuretic 2H-1,2,4-Benzothiadiazine 1,1-Dioxides," *J. Org. Chem.*, 16:815, 1951.

Trapani et al., "Esi Ed Attivita Autimicrobia in vitro di derivati sostitutiti di Fenilpiperidine E Fenilipiperazine," *Il Parmaco. Science*, XL:673-674, 1985.

Tu, "Handbook of Natural Toxins," Mercei Dekker Inc., 1988, N.Y., p. 358.

Waters, Cognitive Enhancing Agents: Current Status in the Treatment of Alzheimer's Disease, *Le Journal Canadien Des Sciences Neurologigues*, 15:249-256, 1988.

Werner et al., "Dihydrobenzothiadiazine 1,1-Dioxides and their Diuretic Properties," *Journal of the American Chemical Society*, 82(5):1161-1166, Mar. 5, 1960.

Kem, "Pyridine Alkaloid Distribution in the Hoplonemetines," *Hydrobiologia*, 156:145-151, 1988.

Kem, "Worm Toxins," *Handbook of Natural Toxins*, 3:353-378, 1988.

Kem, "Biochemistry of Nemertine Toxins," *Marine Pharmacognosy*, Chapter II, 37:84, 1973.

Kem et al., "Hoplonemertine Worms—a New Source of Pyridine Neurotoxins," *Experientia*, 684-686, 1976.

Kem, "A Study of the Occurrence of Anabasine in Paranemertes and Other Nemertines," *Toxicon*, 9:23-32, 1971.

Kem et al., "Isolation and Structure of a Noplonemertine Toxin," *Toxicon*, 9:15-22, 1971.

Kem, "Structure and Action of Nemertine Toxins," *American Zoology*, 25:99-111, 1985.

Leete, "Aberrant Biosynthesis of 5-Fluoroanabasine from 5-Fluoro[5,6-$^{14}$C,$^{13}$C$_2$]nicotinic Acid, Established by Means of Carbon-13 Nuclear Magnetic Resonance," *The Journal of Organic Chemistry*, 44(2):165-168, 1979.

Leete and Chedekel, "The Aberrant formation of (-)-N-methylanabasine From N-Methyl-Δ-Piperideinium Chloride in *Nicotiana Tabacum* and N. *Glauca*, " *Phytochemistry*, 11:2751-2756, 1972.

(List continued on next page.)

Primary Examiner—Ceila Chang
Attorney, Agent, or Firm—Arnold, White & Durkee

[57] ABSTRACT

The invention concerns novel anabaseine-related compounds that are useful in treating certain degenerative neural diseases such as Alzheimer's and Parkinson's which apparently involve decreased function of cerebral cortical nicotinic receptors. The compounds showed activity in both in 'vitro and in active and passive active avoidance studies in animal models. An exemplary active compound is a 3-substituted 2,4-dimethoxy-benzylidene anabaseine.

15 Claims, 3 Drawing Sheets

OTHER PUBLICATIONS

Meyer et al., "Effects of Nucleus Basalis Lesions on the Muscarinic and Nicotinic Modulation of [$^3$H]Acetylcholine Release in the Rat Cerebral Cortex," *Journal of Neurochemistry,* 49(6):1758–1762, 1987.

Nomura et al., "The reaction of 5-benzylidine-2,3,4,5-tetra hyteropyridine with some nucleophiles," *Bull Chem. Society of Japan,* 57:1271, 1984.

Castonquay and Hecht, "Synthesis of Carbon–14 Labeled 4-(Methylnitrosamino)-1-(3-Pyridl)-1-Butanone," *Journal of Labelled Compounds and Radiopharmaceuticals,* 22(1):23–28, Jul., 1984.

Fujisawa et al., "Extension of Bichler Napieralski Reaction," *Chemical Abstracts,* 54(8):185–188, Apr., 1960.

Hu et al., "Chemical Studies on Tobacco Smoke XXIII. Synthesis of Carbon–14 Labelled Myosmine, Nornicotine and N'–Nitrosonornicotine," *Journal of Labelled Compounds,* 10(1):79–89, 1973.

T. Seiyaku, et al., "Novel hetero cyclic compounds", Chemical Abstracts, vol. 59, No. 10, Nov. 11, 1963.

V. Callulo, et al., "Cyclization of –halo nitriles with organo–lithiums", Chemical Abstracts, vol. 113, No. 1, Jul. 2, 1990, pp. 297–301.

"Hackh's Chemical Dictionary", McGraw–Hill Book Co., 1983.

Kem et al. "Occurrence of anabaseine in paranemertes///" CA 74:50957, 1971.

Zoltewicz et al. "Long range transmission . . . " CA 119:49717, 1993.

ANABASEINE DERIVATIVES USEFUL IN THE TREATMENT OF DEGENERATIVE DISEASES OF THE NERVOUS SYSTEM

BACKGROUND OF THE INVENTION

This application is a 371 of PCT/US93/08192 filed Aug. 31, 1993, which is a continuation-in-part of U.S. Ser. No. 07/938,427, filed Aug. 31, 1992, now abandoned.

1. Field of the Invention

This invention relates to novel anabaseine and anabasine derivatives having utility in treating degenerative diseases of the nervous system.

2. Description of the Background Art

It has long been customary in classifying diseases of the nervous system to group them as degenerative, thereby indicating they are characterized by a gradually evolving, relentlessly progressive, neuronal death. Science has shown that a considerable portion of disorders that are classed as degenerative are associated with genetic predisposition which results in a pattern of dominant or recessive inheritance. However, others, although they do not differ in a fundamental way from the hereditary disorders, may occur only sporadically as isolated instances within a given family.

As a consequence, since by definition, classification of degenerative diseases cannot be based upon exact knowledge of their cause or pathogenesis, subdivision of these diseases into individual syndromes rests upon descriptive criteria based largely upon pathologic anatomy and consideration of clinical aspects. As a result, this group of diseases presents itself in the form of several clinical syndromes. However, apart from the general differences that allows the distinction of one syndrome from another, there are certain general attributes which typify this entire class of disorders.

The degenerative diseases of the nervous system can typically be divided into disorders characterized by progressive dementia in the absence of other prominent neurologic signs (e.g., Alzheimer's disease, senile dementia, and Pick's disease); syndromes which combine progressive dementia with other prominent neurologic abnormalities (e.g., Huntington's disease, Hallervorden-Spatz, and progressive familial myoclonic epilepsy); syndromes of gradually developing abnormalities of posture and movement (e.g., Parkinson's disease, striatonigral degeneration, torsion dystonia, and Gilles de la Tourette Syndrome); syndromes of progressive ataxia (e.g., cerebellar cortical degeneration, olivopontocerebellar atrophy, and Friedreich's ataxia); and syndromes of muscular weakness and wasting without motor neuron disease (e.g., amyotrophic lateral sclerosis, spinal muscular atrophy, and hereditary spastic paraplegia), to name but a few.

Among those diseases listed above, perhaps those most familiar are Alzheimer's and Parkinson's diseases. These diseases are progressive neurological disorders characteristically associated with aging. Alzheimer's disease is characterized by a profound loss of memory and other cognitive functions, while Parkinson's disease is an extrapyramidal movement disorder. Both are invariably fatal. Although there is no effective treatment for Alzheimer's disease, clinical trials are underway with several drugs that increase brain cholinergic transmission. In Parkinson's disease, several treatments are temporarily useful, notably L-DOPA related therapies that replace dopamine in the nigrostriatal pathway. However, in Parkinson's disease the therapeutic efficacy of even the best drugs is temporary at best.

Although the loss of neurons in the late stages of Alzheimer's disease is profound, only a few neuronal pathways appear to be affected in its earliest stages. These include cholinergic projections from the nucleus basalis to the cerebral cortex and from the septum to the hippocampus, noradrenergic projections from the locus cerululus to the cerebral cortex, and several peptidergic neurons that are probably intrinsic to the cerebral cortex. The loss of the aforementioned cholinergic pathways in particular is believed to underlie the early memory loss, since these pathways are known to be important for memory and cognition. This association accounts for the major emphasis in novel cholinergic treatments for Alzheimer's disease, at least in its early stages.

A recent study on Alzheimer's disease demonstrated that loss of cholinergic projections from the nucleus basalis to the cerebral cortex was sufficient, after extended intervals, to cause trans-synaptic neuron loss in the rat. Thus, it is conceivable that the early loss of analogous cholinergic neurons in Alzheimer's disease could cause a profound cascade phenomenon resulting in the loss of many neurons over a period of years. If so, then replacement therapy might not only improve survival of these neurons, but perhaps more important, keep other brain cells from dying.

Given the possibility of such therapy, it is of primary importance to determine the type of cholinergic agent most likely to improve memory and/or keep brain neurons from dying after the loss of cholinergic neurons. To address this issue, it is necessary to consider the two general types of cholinergic transmission in the brain. One is termed muscarinic, the other nicotinic. These terms are based on the type of receptor to which acetylcholine binds to in order to elicit its neurotransmitter effect. In brain regions associated with memory, the muscarinic receptors predominate quantitatively over the nicotinic receptors, although both types coexist. For this reason, most investigators traditionally focused on the development of muscarinic agonists to improve memory-related behaviors. These agents have been found to have moderate effects in rats with lesions of the nucleus basalis, but have little effect in patients with pronounced Alzheimer's disease.

There is reason to believe, however, that nicotinic transmission may also be important for treating Alzheimer's disease. This is supported by the fact that cerebral cortical nicotinic receptors decrease significantly during the disease, while post-synaptic muscarinic receptor levels are often unchanged. These observations are consistent with the hypothesis that neurons expressing nicotinic receptors are lost in the disease. When these observations are combined with those of the present inventors, that lesions of ascending cholinergic neurons from the nucleus basalis cause a trans-synaptic neuron loss in the cortex, it is hypothesized that the neurons in the cortex that die trans-synaptically (and in Alzheimer's disease) do so because they do not receive enough nicotinic stimulation. For this reason, the inventors believe nicotinic agents may be useful as replacement therapy for keeping brain neurons alive in Alzheimer's disease that would otherwise die from lack of nicotinic transmission. An analogous situation exists in several other systems such as: (a) muscle cells, which atrophy in the absence of nicotinic activation; (b) sympathetic ganglia, which require either nerve growth factor or nicotinic transmission (in the presence of calcium ions) in order to survive in culture; and (c) nigrostriatal dopamine neurons, which appear to be partially spared by nicotine following lesions of the substantia nigra. Also, it is important to note that there exist several types of nicotinic receptors in the brain, which allows considerable potential selectivity in targeting drugs for certain nicotinic sites.

The observation that nicotine treatment can preserve nigrostriatal dopamine neurons in an animal model for Parkinson's disease is consistent with epidemiological evidence that there is a lower incidence of this disease in cigarette smokers (even after adjusting for the smoking-induced increase in mortality). The mechanism whereby nicotine can preserve these neurons is not known, but it does appear to involve effects of nicotinic transmission on dopamine neurons themselves, since these neurons possess this type of cholinergic receptor. While the remainder of this patent application focuses on the potential treatment of Alzheimer's disease with nicotinic receptor agents, it should be noted that these drugs may be just as effective, or more so, on dopaminergic neurons that are lost in Parkinson's disease.

Nicotine has been used in several clinical trials for the treatment of Alzheimer's disease, primarily over rather short intervals for its potential memory enhancing effect (not for its ability to block long term trans-synaptic cell loss). In one recent study, nicotine had a marginally positive effect on memory and an even greater one of improving the mood of the patients. These positive results have not been followed up with longer term ones, however. Unfortunately, while nicotine has a history of improving memory related behaviors in humans and animals, its potent toxicity, low effective dose range, and peripheral side effects, have basically rendered it unacceptable for treating Alzheimer's disease.

Thus, considerable need exists for agents which stimulate cholinergic transmission, but, unlike nicotine, are relatively non-toxic. The present invention provides novel anabaseine derivatives which have this capability.

SUMMARY OF THE INVENTION

Increased brain neurocortical cholinergic activity is observed with a compound of the formula:

(I)

or a pharmaceutically acceptable salt thereof;
wherein the dotted line between the 1- and 2-positions of the 6-membered cyclic ring containing nitrogen atom represents an optional bond; Y is nitrogen or carbon; $R^1$ is hydrogen or $C_1$–$C_4$ alkyl; and $R^2$ is hydrogen, $C_1$–$C_4$ alkyl, or =CH—X, wherein X is naphthyl optionally substituted by N,N-dialkylamino having 1 to 4 carbons in each of the alkyls, styryl optionally substituted by N,N-dialkylamino having 1 to 4 carbons in each of the alkyls, furyl, furylacrolyl, or wherein $R^3$, $R^4$, and $R^5$ are each selected from hydrogen, $C_1$–$C_4$ alkyl, $C_1$–$C_6$ alkoxy optionally substituted by N,N-dialkylamino having 1 to 4 carbons in each of the alkyls, amino, cyano, N,N-dialkylamino having 1 to 4 carbons in each of the alkyls, halo, hydroxyl, and nitro, provided that $R^1$ and $R^2$ are not hydrogen at the same time, further provided that when there is a double bond between the 1- and 2-positions of the 6-membered cyclic ring containing nitrogen atom of the formula and $R^1$ is hydrogen, $R^2$ is none of 1-methyl, benzylidene and (4-dimethylamino) benzylidene, still further provided that when there is a single bond between the 1- and 2-positions of the 6-membered cyclic ring containing nitrogen atom of the formula and $R^1$ is hydrogen, $R^2$ is not 1-methyl, still further provided that when there is a single bond between the 1- and 2-positions of the 6-membered cyclic ring containing nitrogen atom of the formula and $R^1$ is 2'-methyl, $R^2$ is not hydrogen, and still further that when Y is carbon, $R^2$ is =CH—X.

"Halo" means fluoro, chloro, bromo and iodo. $C_3$–$C_4$ alkyl and $C_3$–$C_6$ alkoxy groups can be straight or branched. Preferably, there is a double bond between the 1- and 2-positions of the 6-membered cyclic ring containing nitrogen atom. Preferably, Y is nitrogen. When $R^1$ or $R^2$ is $C_1$–$C_4$ alkyl, it is preferably methyl. When $R^3$, $R^4$ or $R^5$ is $C_1$–$C_4$ alkyl, it is preferably methyl. When $R^3$, $R^4$ or $R^5$ is $C_1$–$C_6$ alkoxy, it is preferably methoxy.

The present invention also relates to a pharmaceutical composition of the instant compounds and a pharmaceutically acceptable carrier, and a method of treating degenerative neural disease in an animal comprising administering to the animal a therapeutically effective amount of a compound of the present invention.

The above objects, as well as further objects, features and advantages of this invention will be more fully understood by reference to the following detailed description and drawings.

DETAILED DESCRIPTION OF THE INVENTION

Anabaseine, 2-(3-pyridyl)-3,4,5,6-tetrahydropyridine, occurs in certain marine worms, which use the substance to paralyze prey and deter predators (Kern, et al., Toxicon, 9:23, 1971). Anabaseine is a potent activator of vertebrate neuromuscular nicotinic acetylcholine receptors (Kem, Amer. Zoologist, 25:99, 1985). Both nicotine and anabaseine possess a non-aromatic ring attached to the 3-position of a pyridyl ring. Anabaseine's non-aromatic tetrahydropyridine ring imine double bond is conjugated with π-electrons of the 3-pyridyl ring. The imine nitrogen is a much weaker base than the pyrrolidinyl nitrogen of nicotine (Yamamoto, et al., *Agr.Biol.Chem.*, 26:709, 1962). Considerable evidence (Barlow and Hamilton, *Brit.J.Pharmacol*, 18:543, 1962) exists that the non-aromatic ring nitrogen of nicotine must be protonated (cationic) in order to avidly bind to the skeletal muscle nicotinic receptor and activate the opening of its channel. At physiological pH, anabaseine also exists in a hydrolyzed ammonium-ketone form as well as the cyclic imine (unionized) and cyclic iminium (monocationic) forms. The inventors have determined that anabaseine acts as a central nicotinic receptor agonist primarily through its cyclic iminium form. U.S. Pat. No. 5,602,257 assigned to Applicant's assignee, discloses the use of anabaseine, DMAB-anabaseine (also known as 3-[4-(dimethylamino) benzylidene]-3,4,5,6-tetrahydro-2,3'-bipyridine), and anabasine as a nicotine receptor agent, the disclosure of which is incorporated by reference.

Throughout this specification, whenever reference is made to a compound of formula (I) wherein there is a double bond between the 1- and 2-position in the nitrogen-containing 6-membered monocyclic ring, it is to be understood that this also refers to an open (noncyclic) ammonium ketone form corresponding to the cyclic imine or cyclic iminium form of the formula (1).

Thus, for example, the formula (I) embraces both of the following formulae:

The compounds of the formula (I), where there is a double bond between the 1- and 2-positions of the 6-membered ring containing nitrogen, are herein collectively referred to as "anabaseines."

The anabaseines of formula (I) wherein $R^2$ is other than =CH—X may be prepared by a number of routes, including the following route:

In the above formulae, $R^1$ and $R^2$ are as previously defined, and R is a nitrogen-protecting group. The first part of the synthesis of the anabaseines, the joining of an activated derivative of a nicotinic acid or benzoic acid and a modified 2-piperidone, is performed using a mixed Claisen condensation. The second part of the synthesis involves the hydrolysis and decarboxylation of the condensed product.

In the scheme presented herein, certain protecting and activating groups are specifically illustrated. However, one skilled in the art will recognize that other protecting and activating groups could have been used. For example, a variety of amino protecting groups can be used to protect the nitrogen of 2-piperidone (11). Representative amino protecting groups are $C_1$-$C_4$ alkanoyl, benzyl, and trialkylsilyl derivatives such as trimethylsilyl and butyldimethylsilyl. The preferred amino protecting group is trimethylsilyl (TMS). The TMS-protected 2-piperidone (III) is prepared by deprotonation and subsequent reaction with trimethylchlorosilane. Typical silylation conditions are the use of lithium diisopropylamide (LDA) in an inert solvent such as tetrahedrofuran (THF) at −70° C. For each one mole of compound (II), at least one mole of LDA, preferably 1½ moles, should be used to ensure complete silylation. While maintaining the temperature at −70° C., at least one molar equivalent of TMS is combined with the LDA-added reaction mixture. Normally, silylation is complete within a few hours by raising the reaction temperature to ambient temperature.

The protected 2-piperidone (III) is next enolyzed to an enolate by base. Conveniently, this enolization can be conducted by simply adding additional LDA to the reaction mixture containing compound (IV). Although this is a preferred process, other suitable bases which can be employed include metal amides such as $NaNH_2$ or $KNH_2$, metal hydrides such as NaH or KH, and metals such as Na or K. In practice, the reaction mixture is cooled to −70° C., at which point at least one molar equivalent of LDA is added. Enolization is usually complete within an hour, and the resultant amide enolate (IV) can be directly used in the next condensation reaction.

The key Claisen condensation between a 2-piperidone enolate and a nicotinic acid (benzoic acid) derivative can be carried out, e.g., by combining the lithium amide enolate (IV) in an inert solvent such as THF with about one molar equivalent of an ethyl nicotinate analog (or an ethyl benzoate analog) of formula (V). Reaction temperature can be varied, but it is preferred to start the condensation at −70° C. and to allow the temperature to warm up to ambient temperature. Reaction requires a few hours to 24 hours until its completion.

Although an ethyl ester form of compound (V) has been illustrated hereinabove, activation of the carboxylic group to expedite condensation can be achieved by other activating groups known in the art. Especially useful in the herein described condensation are anhydrides, particularly mixed anhydrides, acid halides, and activated esters such as those derived from N-hydroxysuccimide and N-hydroxypthalimide. Alkyl esters of up to $C_5$, other than ethyl ester, can also be used.

The condensed product (VI) is isolated after removal of R (when R is TMS) group by hydrolysis. The product (VI) is normally subjected to hydrolysis and decarboxylation without further purification.

Conversion of compound (VI) to the final anabaseine (VII) is accomplished by first hydrolyzing compound (VI) with a strong acid such as concentrated hydrochloric acid; and second by decarboxylating the intermediate β-keto acid (not shown in the above scheme). Both hydrolysis and decarboxylation steps are conveniently conducted in one-pot in the presence of concentrated hydrochloric acid at an elevated temperature, e.g., under reflux. An anabaseine derivative of formula (VII) or formula (I) is thus obtained as its dihydrochloride.

Alternatively, the anabaseines of the formula (I) wherein $R^2$ is other than =CH—X may be prepared by the following route:

(III) R = TMS   (VIII)

(I)

In the scheme presented above, the protected 2-piperidone (III) is reacted with a pyridyl lithium or phenyl lithium (VIII). Pyridyl lithium (VIII) wherein Y is nitrogen may be prepared from the corresponding bromopyridine [H. Gilman, et al., *J. Org. Chem.*, 16:1485 (1951)]. Typically, the pyridyl lithium (VIII), which is freshly prepared, is used in the condensation in an inert solvent, e.g., dry ether. The reaction is usually complete within a few hours. The reaction mixture (IX) is then acidified and the product (I) is isolated by solvent extraction and purified by, for example, recrystallization.

The compounds of the formula (I) wherein there is a single bond between the 1- and 2-positions of the 6-membered ring containing nitrogen are herein collectively referred to as "anabasines" and they can be obtained by reduction of the corresponding anabaseines.

Reduction of anabaseines to anabasines can be achieved by several ways: (1) Hydrogeneration with hydrogen over Pd/C, as described in E. Spath, et al., *Chem. Ber.*, 69:1082 (1936); (2) Borohydride reduction with either $NaBH_3CN$ or with $NaBH_4$, as described in E. Leete, *J. Org. Chem.* 44:165 (1979); and (3) Reduction with hot formic acid.

The anabasine derivatives of the formula (I) contains an asymmetric center at the 2-carbon of the piperidine ring as indicated below.

Thus, these compounds can exist as an optically active form. The present invention embraces such optically pure anabasines, the pure enantiomers thereof, and the racemate thereof.

The anabasine of formula (I) wherein $R^2$ is 1-methyl can also be prepared by reductive methylation of anabasine. Typically, (S)-anabasine is reacted with a formaldehyde/ formic acid mixture to give 1-methyl-(S)-anabasine. The racemic form of 1-methylanabasine is known (e.g., K. H. Buchel, et al., *Chem. Ber.*, 95:2438, 1962).

The anabaseines of the formula (I) wherein $R^2$ is =CH—X may be prepared from anabaseine. This method is illustrated as follows:

wherein X is as defined previously.

In general, a solution of anabaseine (or its dihydrochloride) in acetic acid is treated with about two molar equivalents of an aldehyde (X—CHO), and the resulting mixture is heated to approximately 60° C. for about 24 hours. The compounds of formula (X) can be isolated and purified by standard techniques such as chromatography and recrystallization.

Although the above acidic reaction conditions are generally satisfactory, basic reaction conditions or buffered conditions are required in the case of the reacting aldehydes bearing an electron-withdrawing group such as nitro. Thus, a basic agent can also be used in the mixed aldol-type condensation.

The compounds of formula (X) wherein X is substituted or unsubstituted phenyl can adopt two conformations about the double bond at the 3-position. Although the formula (XI) depicts an E isomer (which is preferred), a Z isomer also exists as shown below.

Both E and Z isomers are considered to be within the purview of the present invention.

In a manner similar to the conversion of anabaseines of the formula (I) wherein $R^2$ is other than =CH—X, to anabasines of the formula (I), wherein $R^2$ is other than =CH—X, anabasines of the formula (I) wherein $R^2$ is =CH—X can be prepared from anabaseines of the formula (I) wherein reduction $R^2$is =CH—X by reduction. However, due care should be taken in the proposed conversion since catalytic hydrogenation is likely to reduce a double bond at the 3-position as well. Therefore, a borohydride reduction such as that employing sodium borohydride is preferred. The reduction is typically carried out at ambient temperature, with an excess of the hydride agent in, e.g., methanol or ethanol.

The anabasines of formula (I) wherein $R^2$ is =CH—X can be isolated and purified by conventional means, such as recrystallization or chromatography. The present invention includes optically pure forms of the anabasines and the racemic mixture thereof.

The compounds of the formula (I) in their free base form will form acid addition salts, and these acid addition salts are non-toxic and pharmaceutically acceptable for therapeutic use. The acid addition salts are prepared by standard methods, for example by combining a solution of anabaseine or anabasine (base) in a suitable solvent (e.g., water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent or, in the case of aqueous solutions, by lyophilization. Of particular value are the sulfate, hydrochloride, hydrobromide, nitrate, phosphate, citrate, tartrate, pamoate, perchlorate, sulfosalicylate, benzene sulfonate, 4-toluene sulfonate and 2-naphthalene sulfonate salts. These acid addition salts are considered to be within the scope and purview of this invention.

The term "therapeutically effective" means that the amount of the compound of this invention used is of sufficient quantity to increase brain cholinergic transmission. The dosage ranges for the administration of the agent of the invention are those large enough to produce the desired effect in which the nicotinic receptors show some degree of stimulation. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art,. The dosage can be adjusted by the individual physician in the event of any contraindications. Dosage can vary from about 1 µg/kg/dose to about 1000 µg/kg/dose, preferably from about 10 µg/kg/dose to about 500 µg/kg/dose, most preferably from about 30 µg/kg/dose to about 100 µg/kg/dose in one or more dose administrations daily, for one or several days. Alternatively, the dosage can be administered indefinitely in order to prevent a recurrence of cognitive function loss, for example, by administration of the agent in a slow-release form.

The compounds of the invention can be administered parenterally or by gradual perfusion over time. The same agent can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In order to form a pharmaceutically acceptable composition suitable for effective administration, such compositions will contain an effective amount of the compound of this invention, together with a suitable amount of a carrier vehicle.

Additional pharmaceutical methods may be employed to control the duration of action. Controlled release preparations may be achieved by the use of polymers to complex or adsorb the therapeutic agent. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the therapeutic agent into particles of a polymeric material such as polyesters, polyamino acids, hydrogels, poly (lactic acid) or ethylene vinylacetate copolymers. Alternatively, instead of incorporating the therapeutic agent into these polymeric particles, it is possible to entrap the therapeutic agent in microcapsules prepared, for example, by coacervation techniques or by interfacial polymerization, for example, hydroxymethylcellulose or gelatin-microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences (17th Ed., A. Oslo, ed., Mack, Easton, Pa., 1985).

The invention also relates to a method for preparing a medicament or pharmaceutical composition comprising the compound of the invention, the medicament being used for therapy to stimulate brain cholinergic transmission.

The brain neurocortical cholinergic activity of the compounds of the formula (I) is shown by their effectiveness in one or more of the following tests: (a) passive avoidance behavior; (b) active avoidance behavior; (c) frog skeletal muscle contraction; (d) rat colon relaxing properties; (e) neurotransmitter release; and (f) nicotine receptor binding assay.

The above disclosure generally describes the present invention. A more complete understanding can be obtained by reference to the following specific examples which are provided herein for purposes of illustration only, and are not intended to limit the scope of the invention.

EXAMPLE 1

3-Methylanabaseine

3-Methyl-2-piperidone was prepared by methylating the amide enolate ion of 2-piperidone generated with lithium diisopropylamide (LDA) in tetrahydrofuran (THF). The nitrogen atom of 3-methyl-2-piperidone was protected by silyation with trimethylsilyldiethylamine according to the method of K Rulhmann, et al., Chem. Ber., 686:227 (1963). The piperidone was thus heated at reflux for 6 hours with about a 6-fold excess of the silylating agent and then the excess reagent and diethylamine were carefully removed by evaporation under reduced pressure immediately before use with the pyridyl lithium.

3-Pyridyl lithium was prepared from 3-bromopyridine according to the method of H. Gilman, et al., J. Org. Chem., 16:1485 (1951), or of J. Bielawski, et al., J. Heterocycl. Chem., 15:97 (1978). One equivalent of 3-bromopyridine dissolved in dry ether was added dropwise to the dry ice/acetone cooled, dry ethereal solution of 1.1 eq. of BuLi under nitrogen. When all the bromopyridine was added (within ca. 20–25 minutes), the solution containing a lemon precipitate was stirred for another 35–40 minutes before 0.6 eq. of TMS protected 3-methylpiperdone in dry ether was added. After 4 hours of stirring, the cooling bath was removed and the solution was allowed to warm to room temperature. After 3 hours of stirring, 2N HCl was added; 15 minutes later, the phases were separated and the organic phase was discarded. The acidic aqueous layer was adjusted to pH 6–6.5 with $NaHCO_3$, and extracted with ether until no more organic material (monitored by TLC) was found in the extract. After drying ($Na_2SO_4$), the ether was removed, and the title product (39%) was obtained as a yellow oil.

$^{13}$C-NMR (CDCl$_3$/TMS):

δ68.25 (C2), 149.77 (C2' or C6'), 147.48 (C6' or C2'), 134.86 (C3'), 133.89 (C4'), 122.93 (C5'), 50.15 (C6), 29.63 (C3), 27.17 (C5), 19.03 (C4), 18.50 (CH$_3$).

EXAMPLE 2

4-Methylanabaseine and 5-Methylanabaseine

The title compounds were prepared substantially according to the procedure of Example 1, starting with a mixture of 4-methyl- and 5-methyl-2-piperidone. The mixture was prepared by Beckman rearrangement of 3-methylcyclopentanone oxime [L. M. Jackson, et al., J. Org. Chem., 47:1824 (1982)]. An approximately 3:2 ratio of 4-methyl- and 5-methyl-piperidone resulted.

$^{13}$C-NMR of the mixture of the title compounds (CDCl$_3$/TMS) are as follows:

δ163.09 and 162.89 (C2), 150.12 (C2' or C6'), 147.41 (C6' or C2'), 134.86 (C3'), 133.89 (C4'), 122.88 (C5'), 57.39 and 50.19 (C6), 35.10, 29.80, 27.47, 26.98, 26.90, 25.61, 21.69 and 18.89 (CH$_3$).

EXAMPLE 3

4'-Methylanabaseine Dihydrobromide

First, 4-methyl nicotinate was prepared by a modification of the method according to E. Wenkert, et al., Croatica Chem. Acta, 58:737 (1985). Heating was necessary to complete the oxidation reaction. Thus, four g of 3-ethyl-4-methylpyridine (β-collidine) was oxidized with 19 g of KMnO$_4$ in 100 ml water at 70°–75° C. After 2 hours of stirring, the brown MnO$_2$ was removed and the colorless solution was evaporated to a white solid, the salt of the carboxylic acid. This salt then was dissolved in methanol and under ice cooling concentrated sulfuric acid (1.2 eq.) was added. After overnight reflux the methanol was removed by evaporation; aqueous NaHCO$_3$ was added under ice cooling until the pH was slightly basic. Following extraction with ethyl acetate, the organic phase was dried and evaporated to give a pale yellow liquid of the methyl ester with 45% yield.

The Claisen condensation was carried using a flask equipped with a nitrogen inlet. Dry THF (40 mL) was added under nitrogen and cooled to −70° C. in a dry ice/acetone bath before 4.6 mL (7.0 mmol, 1.5 eq) of 1.5M LDA in cyclohexanes (Aldrich) was added. A solution of 0.69 g (7.0 mmol, 1.5 eq) of 2-piperidone in 15–20 mL of dry THF was added all at once to the stirred LDA solution at −70° C. to form the deprotonated amide and then 0.87 mL (6.9 mmol, 1.5 eq) of trimethylsilyl chloride was added through an oven-dried syringe all at once. The resulting solution was stirred (−70° C.) for 15 minutes and at room temperature for 2 hours to form the TMS protected piperidone. The solution turned milky and a solid precipitate formed after a few minutes at −70° C. The precipitate dissolved and the resultant solution was a clear yellow at room temperature. The reaction mixture again was cooled to −70° C., before another 0.69 mL (7.0 mmol, 1.5 eq) of 1.5M LDA was added with stirring to form the protected amide enolate. After 20 minutes, 0.63 g (4.2 mmol, 1 eq) of 3-methylcarboxy-4-methylpyridine (methyl 4-methyl nicotinate) was added; the cooling bath was removed after 20 minutes. Following stirring overnight at room temperature, the precipitate (0.8 g) was collected, dissolved in 15 ml of cc. HBr, heated at reflux for 1 day and then evaporated to dryness. The residue was dissolved in the mixture of methanol and acetone with heating and ethyl acetate then was added until the solution became cloudy. After sitting in the refrigerator for ca. 2 days, 0.62 g (42% yield) of brownish, very hygroscopic solid resulted, m.p. 189°–194° C., dec. $^1$H-NMR of the open-chain hydrolysis product (dihydrobromide), the amino ketone (D$_2$O/DMS); δ1.78 (m, H3, H4), 2.76 (s, Me), 3.04 (tr, J=6.3 Hz, H5), 3.31 (broad, H2), 8.10 (d, H5', J=6.1 Hz), 8.72 (d, H6', J=6.1 Hz), 9.11 (s, H2'). Anal. Calc. for $C_{11}H_{14}N_2 \times 2HBr \times 2H_2O$: C, 35.51; H, 5.42; N, 7.53. Found: C, 35.53; H, 5.02; N, 7.38.

EXAMPLE 4

2'-Methylanabaseine Dihydrochloride

The title compound was prepared substantially according to the procedure of Example 3, employing 3-methylcarboxy-2-methylpyridine. The last hydrolysis and decarboxylation step was carried out in concentrated hydrochloric acid. The product (dihydrochloride) had m.p. 169°–175° C. (dec.). Anal. Calc. for $C_{11}H_{16}N_2O.2HCl.H_2O$: C, 46.79; H, 7.15; N, 9.93. Found: C, 46.49; H, 6.99; N, 10.28.

$^1$H-NMR of the open-chain hydrolysis products (DMSO/DSS): δ1.68 (m, H3, H4), 2.83 (s, CH3), 3.15 (tr, J=6.5 Hz, H5), 3.33 (heptett, J=6.3 Hz, H2), 7.93 (dd, J=8.1 Hz and J=5.9 Hz, H5'), 8.24 (bs, NH), 8.84 (dtr, J=5.7 Hz, H6'), 8.87 (d, J=8.0 Hz, H4'), 8.93 (bs, NH).

EXAMPLE 5

5'-Methylanabaseine

The title compound was prepared substantially according to the procedure of Example 3, employing 3-methylcarboxy-5-methylpyridine.

$^1$H-NMR (CD Cl$_3$/TMS): δ1.74–1.84 (m, H4, H5), 2.25 (s, CH3), 2.26 (m, H3), 3.75 (t, H6, J=5.6 Hz), 7.85 (d, J=1.4 Hz, H4'), 8.36 (S, H6'), 8.65 (d, J=1.9 Hz, H2'). MS(El) m/z 174.1162 (calc. 174.1196).

EXAMPLE 6

6'-Methylanabaseine Dihydrobromide

The title compound was prepared substantially according to the procedure of Example 3, employing 3-methylcarboxy-6-methylpyridine. The product (dihydrobromide) had m.p. 170°–175° C. (dec.). Anal. Calc. for $C_{11}H_{16}N_2O.2HBr.H_2O$: C, 35.51; H, 5.42; N, 7.53. Found: C, 35.29; H, 5.05; N, 7.12.

$^1$H-NMR of the open-chain hydrolysis product (DMSO/DSS): δ1.75 (m, H3, H4), 2.82 (s, CH3), 2.91 (tr, J=6.1 Hz, H5), 3.34 (tr, J=6.3 Hz, H2), 7.93 (bs, NH), 8.02 (dd, J=8.2 Hz and J=2.1 Hz, H5'), 8.83 (dtr, J=8.3 Hz and J=2.1 Hz, H4'), 9.36 (s, H2').

EXAMPLE 7

1-Methyl-(S)-Anabasine Dihydrobromide

The title compound was prepared by Eschweiler-Clarke reductive ethylation of (S)-anabasine. A solution of 0.253 g (1.56 mmol) of (S)-anabasine, 500 μL of 37% formaldehyde, and 0.75 mL of 90% formic acid was heated on a steam bath for 7.5 hours. The mixture was diluted with aqueous Na$_2$CO$_3$ until the pH was basic and extracted with diethyl ether. The ether phase was dried over Mg$_2$SO$_4$ and evaporated to yield 0.238 g (87% yield) of (S)-1-methyl-anabasine as a yellow liquid. The 1H-NMR spectrum of this yellow liquid was consistent with the product. The dihydrobromide salt of (S)-1-methylanabaseine was prepared by dissolving the free base in isopropyl alcohol, acidifying the solution with concentrated HBr, and evaporating the solvent to a solid. The solid dihydrobromide salt was recrystallized from methanol and isopropyl alcohol to yield 0.142 g (27% yield) of small white needle-like crystals (red 210°–215° C. decomp). Anal. Calc. for $C_{11}H_{16}N_2.2HBr.½H_2O$: C, 38.07; H, 5.52; N, 8.07. Found: C, 38.11; H, 5.47; N, 7.80.

EXAMPLE 8

3-[(4-Nitro)benzylidene)anabaseine

Anabaseine dihydrochloride was dissolved in an aqueous mixture of 0.6M acetic acid/0.2M sodium acetate along with two equivalents of p-nitrobenzaldehyde. The volume is such that the concentration of acetic acid is 2.5 times that of the anabaseine. After heating for about 24 hours at approximately 60° C., the mixture was diluted with twice its initial volume of water and with twice its initial volume of concentrated brine to precipitate the excess aldehyde. Additional aldehyde was removed by 2–3 extractions with ethyl acetate, with a volume about one-half that of the aqueous phase. Solid Na$_2$CO$_3$ was added and the alkaline solution was extracted again with ethyl acetate. Drying and evaporating the ethyl acetate gave an oil (70%) that solidified by scratching with some cyclohexane. Recrystallization gave a pale yellow product, top, 125°–128° C. Anal. Calc. for $C_{17}H_{15}N_3O_2$: C, 69.61; H, 5.15; N, 14.33. Found: C, 69.18; H, 5.10; N, 14.12.

$^1$H-NMR (CDCl$_3$/TMS): δ1.87 (m, H5), 2.82 (t, H4), 3.94 (t, H6), 7.45, 8.23 (arom.), 6.70 (vinyl), 7.36 (H5'), 7.85 (H4'), 8.67 (H6'), 8.76 (H2').

EXAMPLE 9

3-[(2,4-Dichloro)benzylidene]anabaseine Dihydrochloride

The title compound was prepared substantially according to the procedure of Example 8 by reaction of anabaseine dihydrochloride with 2,4-dichlorobenzaldehyde. The resulting product (free base) was dissolved in ether, and precipitated with ether/HCl to provide the title compound as a beige solid, m.p. 238°–242° C. (dec.).

$^1$H-NMR of the free base of the title compounds (CDCl$_3$/TMS): δ8.78 (s, H2'), 8.647 (d, 4.83 Hz, H6'), 7.865 (d, 7.73 Hz, H4'), 7.425 (s, H7), 7.353 (dd, 7.8, 4.80 Hz, H5'), 6.692 (s, H9), 3.925 (t, 5.62 Hz, H6), 2.627 (t, 5.71 Hz, H4), 1.841 (quintet, 5H).

EXAMPLE 10

3-[(4-Chloro)benzylidene]anabaseine

The title compound was prepared substantially according to the procedure of Example 8 by reaction of anabaseine dihydrochloride with 4-chlorobenzaldehyde.

$^1$H-NMR (CDCl$_3$/TMS): δ1.84 (m, H5), 2.80 (t, H4), 3.89 (t, H6), 7.23, 7.34 (aromatic), 6.60 (vinyl), 7.3 (H5'), 7.82 (H4'), 8.67 (H6'), 8.74 (H2').

EXAMPLE 11

3-[(4-Cyano)benzylidene]anabaseine

The title compound was prepared substantially according to the procedure of Example 8 by reaction of anabaseine dihydrochloride with 4-cyanobenzaldehyde.

$^1$H-NMR (CDCl$_3$/TMS): δ1.85 (m, H5), 2.80 (t, H4), 3.93 (t, H6), 7.38, 7.65 (aromatic), 6.64 (vinyl), 7.36 (H5'), 7.83 (H4'), 8.66 (H6'), 8.75 (H2').

EXAMPLE 12

3-[(2,4-Dimethoxy)benzylidene]anabaseine Dihydrochloride

The title compound was prepared substantially according to the procedure of Preparation 2 by reaction of anabaseine dihydrochloride with 2,4-dimethoxybenzaldehyde. This afforded the title compound as a yellow solid (89%), m.p. 225°–230° C. (dec).

$^1$H-NMR (DMSO-D$_6$): δ8.94 (cl, 1.5 Hz, H2'), 8.92 (dd, 7.4 and 1.7 Hz, H6'), 8.22 (dr, 8.6, 2.1, 1.92, H4'), 7.79 (dd, 7.90. 5.10 Hz, H5'), 7.60 (d, 8.8, H13), 7.31 (s, H10), 6.70 (dd, 8.8, 2.4 Hz, H12), 6.65 (s, H7), 3.85 (s, OMe), 3.80 (t, 5.7 Hz, H6), 3.72 (s, OMe), 2.92 (t, 5.66 Hz, H4), 2.02 (quintet, H5). Anal. Calcd. for $C_{19}H_{22}N_2O_2Cl_2$: C, 59.85; H, 5.82; N, 7.35. Found: C, 59.54; H, 5.89; N, 7.41.

EXAMPLE 13

3-[(2,4-Dimethyl)benzylidene]anabaseine Dihydrochloride

The title compound was prepared substantially according to the procedure of Preparation 2 by reaction of anabaseine dihydrochloride with 2,4-dimethylbenzaldehyde. This afforded the title compound as a bright yellow solid, m.p. 235°–238° C. (dec).

$^1$H-NMR ($D_2O$/DSS): δ9.01 (d, H6'), 8.99 (d, 1.4 Hz, H2'), 8.54 (dr, 8.2, 1.4 Hz, H4'), 8.04 (dd, 8.1, 5.4 hz, H5'), 7.45 (s, H7), 7.41 (s, H10), 7.40 (d, 7.3 Hz, H13), 7.20 (d, 7.4 Hz, H12), 3.96 (t, 5.7 Hz, H6), 2.96 (t, 6.1 Hz, H4), 2.34 (s, Me), 2.14 (t, 5.7 Hz, H5), 2.10 (s, Me). Anal. Calcd. for $C_{19}H_{22}N_2Cl_2 \times H_2O$: C, 62.13, H, 6.59, N, 7.61. Found: C, 62.21; H, 6.78; N, 7.21.

EXAMPLE 14

3-[(2,4,6-Trimethyl)benzylidene]anabaseine Dihydrochloride

The title compound was prepared substantially according to the procedure of Preparation 2 by reaction of anabaseine dihydrochloride with 2,4,6-trimethylbenzaldehyde. This afforded the title compound as an off-white product, m.p. 228°–232° C. (dec).

$^1$H-NMR (DMSO-$d_6$/DSS): δ9.01 (s, H2'), 8.98 (d, 4.97 Hz, H6'), 8.30 (d, 7.62 Hz, H4'), 7.82 (td, 7.71, 5.10 Hz, H5'), 7.28 (s, H7), 6.96 (s, H10, H12), 3.87 (t, 5.8 Hz, H6), 2.36 (t, 6.0 Hz, H4), 2.27 (s, Me, 3H), 2.13 (s, Me, 6H), 1.99 (t, H5). Anal. Calcd. for $C_{20}H_{24}N_2Cl_2 \cdot 0.5 H_2O$: C, 64.47; H, 6.76; N, 7.52. Found: C, 64.00; H, 6.96; N, 7.45.

EXAMPLE 15

3-[(2,4-Dimethoxy)benzylidene]-2-phenyl-3,4,5,6-tetrahydropyridine Dihydrochloride The title compound was prepared substantially according to the procedure of Preparation 2 by reaction of 2-phenyl-3,4,5,6-tetrahydropyridine (Preparation 1) with 2,4-dimethoxybenzaldehyde. This afforded the title compound as a yellow hygroscopic salt (87%).

$^1$H-NMR (CDCl$_3$/TMS): δ7.75(d), 7.46(d), 7.30(m), 7.20 (d), 6.78(s), 6.52(d), 6.39(s), 3.78(s), 3.72(t), 3.66(s), 2.68 (t), 1.72(q). MS(FAB) (M+H)$^+$ 307.

EXAMPLE 16

3-[(2,4-Dimethoxy)benzylidene]-1-methylanabaseine Trifluoroacetate

The title compound was prepared substantially according to the procedure of Preparation 2 by raction of 1-methylanabaseine dihydrochloride with 2,4-dimethoxybenzaldehyde. This afforded the title compound after preparative HPLC on Vydac C$_4$ eluted with acetonitrile containing 0.1% trifluoroacetic acid.

$^1$H-NMR (CD$_3$OD): δ8.88 (d, J=4.0 Hz, H6'), 8.68 (S, H2'), 8.01 (d, J=7.6 Hz, H4'), 7.74 (dd, J=7.7 Hz, 5.3 Hz, H5'), 7.58 (d, J=9.0 Hz, H13), 7.21 (s, H7), 6.68 (d, J=8.7, H12), 6.56 (s, H10), 4.03 (t, J=5.9 Hz, H6), 3.87 (s, OMe), 3.69 (s, OMe), 3.34 (s, NMe), 3.01 (t, J=5.7 Hz, H4), 2.20 (q, J=6.0 Hz, H5).

EXAMPLE 17

3-[(2,4-Dimethoxy)benzylidene]-6'-methyl anabaseine Dihydrochloride

The title compound was prepared substantially according to the procedure of Preparation 2 by reaction of 6'-methylanabaseine dihydrochloride with dimethoxybenzaldehyde. This afforded the title compound as a yellow hygroscopic salt (90%).

$^1$H-NMR (DMSO/TMS): δ8.62 (s, H2'), 7.90 (d, J=0.3 Hz, H4'), 7.51 (d, J=8.1 Hz, H5'), 7.46 (d, J=8.7 Hz, H13), 7.12 (s, H7), 6.64 (d, J=8.90, H12), 6.60(s, H10), 3.82 (s, OMe), 3.75 (tr, J=5.3 Hz, H6), 3.70 (s, OMe), 2.82 (tr, J=5.1 Hz, H4), 1.90 (qn, J=5.2 Hz, H5), MS(FAB) (M+H)$^+$ 322.

EXAMPLES 18–30

By reaction of anabaseine dihydrochloride with 4-methylbenzaldehyde, 4-aminobenzaldehyde, 4-hydroxybenzaldehyde, 4-diethylaminobenzaldehyde, 4-hydroxyl-3-methoxy-benzaldehyde, 2-methoxybenzaldehyde, 3-methoxybenzaldehyde, 4-methoxybenzaldehyde, 2,4,6-trimethoxybenzaldehyde, 2-hydroxyl-4-methoxybenzaldehyde, 2,4-dihydroxylbenzaldehyde, and 4-hydroxyl-2-methoxybenzaldehyde, respectively, using the procedure of Preparation 2 the following compounds were obtained 3-[(4-methyl)benzylidene]anabaseine (18)

$^1$H-NMR (CDCl$_3$): δ8.75 (H2'), 8.63 (H6'), 7.82 (H4'), 7.33 (H5'), 7.19 (aromatic), 6.62 (vinyl), 3.87 (H6), 2.84 (H4), 2.35 (CH$_3$), 1.82 (H5).

3-[(4-amino)benzylidene]anabaseine (19)

$^1$H-NMR (CDCl$_3$): δ8.73 (H2'), 8.62 (H6'), 7.81 (H4'), 7.32 (H5'), 7.15, 6.65 (aromatic), 6.53 (vinyl), 3.84 (H6), 2.84 (H4), 1.83 (H5).

3-[(4-hydroxyl)benzylidene]anabaseine (20)

$^1$H-NMR (CD$_3$OD): δ8.62 (H2'), 8.50 (H6'), 7.90 (H4'), 7.53 (H5'), 7.26, 6.79 (aromatic), 6.54 (vinyl), 3.78 (H6), 2.88 (H4), 1.87 (H5).

3-[(4-diethylamino)benzylidene]anabaseine (21)

$^1$H-NMR (CDCl$_3$): δ8.73 (H2'), 8.62 (H6'), 7.82 (H4'), 7.32 (H5'), 7.23, 6.63 (aromatic), 6.55 (vinyl), 3.83 (H6), 3.38 (CH$_2$), 2.88 (H4), 1.85 (H5), 1.18 (CH$_3$).

3[(4-dimethylaminopropoxy)benzylidene]anabaseine (22)

$^1$H-NMR (CDCl$_3$/TMS): δ8.71 (H2'), 8.62 (H6'), 7.81 (H4'), 7.3 (H5'), 7.24, 6.87 (aromatic), 6.56 (vinyl), 4.03 (OCH$_2$), 3.86 (H6), 2.82 (H4), 2.50 (NCH$_2$), 2.23 (Me), 1.98 (CH$_2$), 1.82 (H5).

3-[(4-hydroxy-3-methoxy)benzylidene]anabaseine (23)

$^1$H-NMR (CDCl$_3$): δ8.74 (H2'), 8.63 (H6'), 7.83 (H4'), 7.34 (H5'), 6.89, 6.76 (aromatic), 6.57 (vinyl), 3.87 (OCH$_3$), 3.86 (H6), 2.85 (H4), 1.84 (H5).

3-[(2-methoxy)benzylidene]anabaseine (24)

$^1$H-NMR (ClCl$_3$): δ8.79 (H2'), 8.62 (H6'), 7.86 (H4'), 7.30 (H5'), 6.97, 6.87 (aromatic) 6.83 (vinyl), 3.91 (H6), 3.76 (OCH$_3$), 2.74 (H4), 1.82 (H5).

3-[(3-methoxy)benzylidene]anabaseine (25)

$^1$H-NMR (CDCl$_3$): δ8.76 (H2'), 8.64 (H6'), 7.83 (H4'), 7.33 (H5'), 6.86, 7.28 (aromatic), 6.63 (vinyl), 3.89 (H6), 3.80 (OCH$_3$), 2.84 (H4), 1.83 (H5).

3-[(4-methoxy)benzylidene]anabaseine (26)

$^1$H-NMR (CDCl$_3$): δ8.74 (H2'), 8.63 (H6'), 7.82 (H4'), 7.33 (H5'), 7.26. 6.89 (aromatic), 6.59 (vinyl), 3.86 (H6), 3.82 (OCH$_3$), 2.84 (H4), 1.83 (H5).

3-[(2,4,6-trimethoxy)benzylidene]anabaseine (27)

¹H-NMR (CDCl₃): δ8.81 (H2'), 8.60 (H6'), 7.89 (H4'), 7.30 (H5'), 6.13 (aromatic), 6.47 (vinyl), 3.70 (OCH₃), 3.80 (OCH₃), 3.80 (H6), 2.80 (H4), 1.80 (H5).

3-[(2-hydroxyl-4-methoxy)benzylidene]anabaseine dihydrochloride (28)

¹H-NMR (DMSO): δ8.80 (bd, J=4.9 Hz, H6'), 8.82(s, H2'), 8.10 (dd, J=7.5 Hz and J=1.5 Hz, H4'), 7.71 (dd, J=7.5 Hz and J=4.5 Hz, H5'), 7.59 (d, J=9.0 Mz, H13), 7.41 (s, H7), 6.58 (d, J=8.6 Hz, H12), 6.52 (s, H10), 3.77 (s, OMe), 3.61 (tr, J=5.5 Hz, H6), 2.94 (tr, J=5.2 Hz, M4), 2.03 (qn, J=5.1 Hz, H5).

3-[(2,4-dihydroxyl)benzylidene]anabaseine dihydrochloride (29)

¹H-NMR (DMSO): δ8.86 (dd, J=5.10, Hz, H6'), 8.79 (bs, H2'), 8.05 (d, J=7.89 Hz, H4'), 7.66 (dd, J=7.74 Hz and 4.89 Hz, H5'), 7.51 (d, J=9.0 Hz, H13), 7.42 (s, H7), 6.39 (broad, H12 and N⁺H), 6.32 (s, H10), 3.78 (tr, J=5.40 Hz, H6), 2.92 (tr, J=5.76 Hz, H4), 2.02 (qn, J=5.10 Hz, H5).

3-[(4-hydroxyl-2-methoxy)benzylidene]anabaseine dihydrochloride (30)

¹H-NMR (DMSO-d₆): δ8.89 (d, J=4.9 Hz, H2'), 8.83 (d, J=1.8 Hz, H6'), 8.11 (d, J=9.8 Hz, H4'), 7.71 (dd, J=5.5 Hz and 4.8 Hz, H5'), 7.54 (d, J=8.8 Hz, H13), 7.36 (s, H7), 6.57 (d, J=10.8 Hz, H12), 6.49 (d, J=2.3 Hz, H10), 3.78 (tr, J=5.4 Hz, H6), 3.65 (s, OMe), 2.93 (tr, J=5.3 Hz, H4), 2.03 (tr, J=5.4 Hz, M5), 10.39 (br, N₁H⁺), 12.40 (br, N₂M⁺).

EXAMPLE 31

General procedure for alkylation of 2,4-dihydroxybenzaldehyde and condensation with anabaseine To 1 eq of 2,4-dihydroxybenzaldehyde dissolved in dry alcohol, (e.g., methanol, ethanol) 2.1 eq of KOH was added. The deep red solution was stirred in insert atmosphere (the starting aldehyde is sensitive even to moisture) at 75°–80° C. for ca. 20 min. then 2.4 eq of alkylhalogenide was added. The solution was stirred at this temperature for ca. 1 day, then evaporated to dryness. The solid residue was extracted with water/ethyl acetate. The organic layer was discarded and the aqueous layer was made acidic and extracted with ethyl acetate, several times. The combined organic layer was dried and evaporated to a deep red, oily material which was analyzed by MS and NMR spectroscoies. This crude reaction mixture was used for the condensation with anabaseine without any further purification. After condensation, the compounds were purified by preparative HPLC method on Vydac C4, preferably eluted with acetonitrile containing 0.1% trifluoroacetic acid.

EXAMPLE 32

3-[(2,4-Dipropoxy)benzylidene]anabaseine

The title compound was prepared substantially according to the procedure of Example 31 by reaction of anabasine dihydrochloride with 2,4-dipropoxybenzaldehyde.

¹H-NMR (CDCl₃): δ8.73 (s, H2'), 8.60 (d, J=4.80 Hz, H6'), 7.80 (dd, J=7.4 Hz and 4.9 Hz, H4'), 7.29 (m, H5 and H13), 6.85 (s, H7), 6.44 (d, J=9.0 Hz, H12), 6.38 (s, H10), 3.92 (q, J=6.4 Hz, CH₂ of Pr), 3.87 (tr, J=5.4 Hz, H6), 3.83 (tr, J=6.2 Hz, CH₂ of Pr), 2.78 (tr, J=4.9 Hz, H4), 1.88 (m, H5 and CH₂ of Pr), 1.68 (qn, J=7.0 Hz, CH₂ of Pr), 1.04 (tr, J=7.3 Hz, CH₃ of Pr), 0.85 (tr, J=7.3 Hz, CH₃ of Pr). MS(FAB) (M+H)⁺ 365.

EXAMPLE 33

3-[(2,4-Diisopropoxy)benzylidene]anabasine trifluoroacetate

The title compound was prepared substantially according to the procedure of Example 31 by reaction of anabasine dihydrochloride with 2,4-diisoproxybenzaldehyde.

¹H-NMR (CD₃OD): δ8.90 (d, J=4.8 Hz, H6'), 8.81 (s, H2'), 8.00 (d, J=7.8 Hz, H4'), 7.71 (dd, J=7.8 Hz and 4.8 Hz, H5'), 7.68 (d, J=8.7 Hz, H13), 7.43 (s, H7), 6.66 (d, J=9.0 Hz, H12), 6.62 (s, H10), 4.78 (q, J=6.0 Hz, CH of iPr), 4.63 (q, J=6.0 Hz, CM of iPr), 3.78 (tr, J=5.5 Hz, H6), 2.96 (tr, J=5.4 H4), 2.05 (qn, J=5.1 Hz, H5), 1.28 (d, J=6.0 Hz, CH3 of iPr), 1.03 (d, J=6.2 Hz, CH3 of iPr). M3(FAB) (M+H)⁺ 365.

EXAMPLE 34

3-[(2-Hydroxy-4-isopropoxy)benzylidene]anabaseine trifluoroacetate

The title compound was prepared substantially according to the procedure of Example 31 by reaction of anabaseine dihydrochloride with 2-hydroxy-4-isopropoxybenzaldehyde.

¹H-NMR (CD₃OD): δ8.88 (d, J=4.8, Hz, H6'). 8.79 (s, H2'), 8.06 (dd, J=7.8 Hz and 1.9 Hz, H4'). 7.71 (m, H13 and H5'), 7.66 (s, H7), 6.53 (d, J=8.7 Hz, H12), 6.53 (s, H10), 4.52 (q, J=6.0 Hz, CH of iPr), 3.84 (tr, J=5.5 Hz, H6), 3.07 (tr, J=5.4, H4), 2.16 (qn, J=5.8 Hz, H5), 1.13 (d, J=6.0 Hz, CH₂ of iPr). MS(FAB) (M+H)⁺ 323.

EXAMPLE 35

3-[(2,4-Dipentoxy)benzylidene]anabaseine trifluoroacetate

The title compound was prepared substantially according to the procedure of Example 31 by reaction of anabaseine dihydrochloride with 2,4-dipentoxybenzaldehyde.

¹H-NMR (CD₃OD): δ8.87 (d, J=4.6 Hz, H6'), 8.79 (s, H2'), 8.08 (dd, J=7.2 Hz and 1.5 Hz, H4'), 7.74–7.68 (m, H5', H13, H7), 6.69 (d, J=9.0 Hz, H12), 6.54 (s, H10), 4.06 (tr, J=6.0 Hz, CH₂ of pentyl), 3.91 (tr, J=6.2 Hz, CH₂ of pentyl), 3.86 (tr, J=4.8 Hz, H6), 3.08 (tr, J=4.7 Hz, H4), 2.18 (tr, J=4.8 Hz, H5), 1.79–1.10 (overlapping multiplet, rest of the CH₂ of pentyl), 0.94 (tr, J=6.9 Hz, CH3 of pentyl), 0.87 (tr, J=7.2 Hz, CH₃ of pentyl). MS(FAB) (M+H)⁺ 421.

EXAMPLE 36

3-[(2-Hydroxy-4-pentoxy)benzylidene]anabasine trifluoroacetate

The title compound was prepared substantially according to the procedure of Example 31 by reaction of anabaseine dihydrochloride with 2-Hydroxy-4-pentoxybenzaldehyde.

¹H-NMR (CD₂OD): δ8.86 (dd, J=4.8 Hz and 1.5 Hz, H6') 8.79 (d, J=1.5 Hz, H2'), 8.05 (dd, J=7.8 Hz and 1.8 Hz, H4'), 7.66 (dd, J=7.4 Hz and 5.1 Hz, H5'). 7.62 (d, J=9.0 Hz, H13), 7.46 (s, H7), 6.55 (d, J=9.0 Hz, H12), 6.42 (s, H10), 3.88 (tr, J=6.0 Hz, CH₂ of pentyl), 3.77 (tr, J=4.8 Hz, H6), 2.95 (tr, J=4.7 Hz, H4), 2.04 (tr, J=4.80 Hz, H5), 1.44 (qn, J=6.0 Hz, CH2 of pentyl), 1.5 (qn, J=6.0 Hz, CH₂ of pentyl), 0.99 (qn, J=6.9 Hz, CH₃ next to CH₃ of pentyl), 0.81 (tr, J=7.2 Hz, CH3 of pentyl). MS(FAB) (M=H)⁺ 351.

EXAMPLE 37

3-[(4-Dimethylamino)cinnamylidene]anabaseine Dihydrochloride

The title compound was prepared substantially according to the procedure of Preparation 2 by reaction of anabaseine dihydrochloride with p-dimethylaminocinnamaldehyde, except that a mixture of the two reagents was heated at reflux overnight. This afforded the title compound as a black semi-solid, m.p. 115°–120° C. (dec).

¹H-NMR (DMSO-d₆): δ9.02 (dd, 5.4 and 1.5 Hz H6'), 8.99 (d, 1.7 Hz, H2'), 8.39 (dt, 8.1, 1.7 Hz, H4'), 7.97 (dd, 8.0, 5.1 Hz, H5'), 7.75 (d, 9.0 Hz, 2H), 7.28 (dd, 15.0, 10.0 Hz, H8), 7.24 (d, 15.0 Hz, H9), 7.00 (d, 10.3 Hz, H7), 6.86 (d, 8.8 Hz, 2H), 3.74 (t, 5.55 Hz, H6), 3.03 (s, N—Me₂), 2.86 (t, 5.8 Hz, H4), 2.03 (t, 5.8 Hz, H5). Anal. catcd. for $C_{21}H_{23}N_3 \cdot 3HCl \cdot 3.5H_2O$: C, 51.49; H, 6.79. Found: C, 51.81; H, 6.65.

EXAMPLE 38–41

By reaction of anabaseine dihydrochloride with 2-furaldehyde, 3-furaldehyde 2-furanacrolein and, 4-dimethylamino-1-naphthylaldehyde, respectively, using the procedure of Preparation 2, the following compounds were obtained 3-(2-furylidene) anabaseine (38)

¹H-NMR (DMSO-d₆): δ8.63 (d, J=1.56 Hz, H6'), 8.80 (d, J=2.01 Hz, H2'), 7.85 (d, J=9.7 Hz, H4'), 7.46 (dd, J=4.9 Hz and 5.1 Hz, H5'), 6.34 (d, J=7.5 Hz, H9), 7.81 (s, H7), 6.75 (d, J=3.42 Hz, H11), 6.63 (dd, J=3.54 and J=5.25 Hz, H10), 6.34 (d, J=5.4 Hz, H9), 3.70 (tr, J=10.92 Hz, H6), 2.93 (m, J=14.61 Hz, H4), 2.01 (tr, J=13.02 Hz, H5).

3-(3-furylidene) anabaseine (39)

¹H-NMR (DMSO-d₆): δ8.63 (d, J=1.58 Hz, H6'), 8.60 (d, J=3.18 Hz, H2'), 7.96 (s, H12), 7.82 (d, J=11.73 Hz, H4'), 7.73 (s, H7), 7.44 (dd, J=5.64 Hz and 5.67 Hz, H5'), 6.70 (d, J=1.71 Hz, H10), 6.41 (d, H4), 1.74 (tr, J=17.76 Hz, H5).

3-(2-furyl-3-propenylidene)anabaseine (40)

¹H-NMR (DMSO-d₆): δ8.61 (d, J=4.7 Hz, H6'), 8.57 (d, J=2.2 Hz, H2'), 7.78 (d, J=9.7 Hz, H4'), 7.44 (dd. J=4.8 Hz and 4.9 Hz, H5'), 7.71 (s, H7), 6.95 (dd, J=11.4 Hz and 11.2 Hz, H8) 6.65 (d, J=15.6 Hz, H13), 6.55 (m, J=12.6 Hz, H12), 6.25 (d, J=11.2 Hz, H11), 3.75 (tr, J=10.8 Hz, H6), 2.69 (m, J=12.5 Hz, H6), 1.74 (tr, J=12.3 Hz, H9).

3-(4-dimethylamino-1-napthylidene)anabaseine (41)

¹H-NMR (DMSO-d₆): δ8.77 (d, J=1.95 Hz, H2'), 8.63 (d, J=4.68 Hz, H6'), 8.18 (d, J=7.5 Hz, H9), 7.98 (d, J=7.86 Hz, H10), 7.65 (d, J=4.29 Hz, H4'), 7.51 (dd, J=8.68 Hz, H5'), 7.48 (d, J=25.35 Hz, H14, H15, H16), 7.12 (d, J=7.8 Hz, H13), 6.99 (s, H7), 6.41 (d, J=5.4 Hz, H9), 3.83 (tr, J=11.13 Hz, H6), 2.84 (s, NMe₂), 2.62 (m, J=10.32 Hz, H4), 1.71 (tr, J=12.33 Hz, H5).

EXAMPLE 42

3-[(4-Dimethylamino)benzylidene]-2-(3-pyridyl)-piperidine

The title compound was prepared from the corresponding 3-benzylideneanabaseine using borohydride according to the method of E. Leete in *J. Org. Chem.*, 44, 165 (1979).

¹H-NMR (CDCl₃/TMS): δ8.70 (d, H2'), 8.53 (dd, H6'), 7.83 (dr, H4'), 7.30 (dd, H5'), 7.08, 6.69 (d, aromatic), 5.91 (s, vinyl), 4.50 (s, H2), 2.94 (s, Me), multiplets at 3.05, 2.65, 1.8, 1.7 for H4, H5 and H6.

EXAMPLE 43

3[(2,4-Dimethoxy)benzylidene]-2-(3-pyridyl)-piperidine

The title compound was prepared substantially according to the procedure of E. Leete in *J. Org. Chem.*, 44:165 (1979), starting with the corresponding 3-benzylideneanabaseine. This afforded the title compound.

¹H-NMR (CDCl₃): δ8.71 (S, H2'), 8.50 (d, H6', J=3.83 Hz), 7.85 (d, H4', J=7.8 Hz), 7.25 (dt, H5', J=7.8 Hz and J=3.8 Hz), 7.05 (d, Ar, J=7.9 Hz), 6.45 (d, Ar, J=8.0 Hz), 6.42 (s, vinyl), 5.97 (s, Ar), 4.52 (s, H2), 3.78 (s, OMe), 3.73 (s, OMe), 2.99–2.89 (m, H6), 2.45–2.43 (m, H4), 1.67 (tr, H5, J=5.6 Hz).

EXAMPLE 44

Nicotine Receptor Binding

Nicotine receptor binding can be measured as described in Abood, et al., *Biochem Pharmacol.*, 35:4199, 1986, or in Boksa, et al., *Eur. J. Pharmacol*, 139:323, 1987. In essence, washed rat cerebral cortex membranes suspended in ice-cold saline (pH 7.4) is incubated with [³H]-N-methylcarbamyl choline (³H—MCC) for 60 minutes before being washed free of unbound radioligand with two rapid washes of the saline solution, using vacuum filtration. The glass filters used to collect the membranes for scintillation counting are pre-equilibrated with polyethyleneimine to reduce ligand binding by the filters.

Atropine sulfate at 1.2 μM is used to block muscarinic binding sites. Non-specific binding is assessed in the presence of 100 μM carbamylcholine. Thus, the KD values of the test compounds are determined by their ability to compete for [³-H-acetyl]choline or ³H—MCC binding. The apparent $K_i$ values were calculated from the Cheng-Prusoff equation assuming a KD for [³H]—MCC of 5 nM. Some representative compounds of this invention were tested for their ability to displace [³H]MCC. Results are indicated in Table 1. The $K_i$ values presented in the table are mean values obtained from two separate experiments.

TABLE 1

| COMPOUND | KI (μM) |
| --- | --- |
| EXAMPLE 3 | 3.8 |
| EXAMPLE 4 | 33 |
| EXAMPLE 5 | 0.13 |
| EXAMPLE 6 | 0.026 |
| EXAMPLE 7 | 1.2 |
| EXAMPLE 8 | >5 |
| EXAMPLE 9 | 2.0 |
| EXAMPLE 10 | >5 |
| EXAMPLE 11 | >5 |
| EXAMPLE 12 | 0.12 |
| EXAMPLE 13 | 1.0 |
| EXAMPLE 14 | 0.5 |
| EXAMPLE 15 | >5 |
| EXAMPLE 16 | >5 |
| EXAMPLE 17 | 0.50 |
| EXAMPLE 18 | 2.0 |
| EXAMPLE 19 | 0.17 |
| EXAMPLE 20 | 0.025 |
| EXAMPLE 22 | 1.6 |
| EXAMPLE 23 | >5 |
| EXAMPLE 24 | 0.83 |
| EXAMPLE 25 | 4.0 |
| EXAMPLE 26 | 0.32 |
| EXAMPLE 27 | 0.17 |
| EXAMPLE 28 | 1.5 |
| EXAMPLE 29 | 0.45 |
| EXAMPLE 32 | 4.5 |
| EXAMPLE 33 | 1.0 |
| EXAMPLE 35 | 2.5 |
| EXAMPLE 36 | 0.25 |
| EXAMPLE 37 | 0.40 |
| EXAMPLE 38 | 0.64 |
| EXAMPLE 39 | 0.86 |
| EXAMPLE 40 | 0.80 |
| EXAMPLE 42 | 5.0 |
| EXAMPLE 43 | 3.2 |

These results show that the compounds tested bind to rat brain synaptosome high affinity brain nicotinic receptors.

EXAMPLE 45

RAT COLON MYENTERIC PLEXUS; MUSCLE BIOASSAY

The distal segment of the rat colon was dissected free of circular muscle, leaving the longitudinal muscle and its myenteric plexus innervation. This preparation was mounted in a 10 ml tissue bath containing a rat colon saline (Romano, 1981) which was continuously oxygenated. The muscles were suspended at a length providing about 0.5 g resting tension. Contractions in response to 320 nM oxotremorine (muscarinic agonist) were recorded isometrically using a Grass strain gauge-polygraph system. The ability of test compounds to relax the oxotremorine contraction was assessed by adding it to the bath once the peak of contraction had been reached. The potency of the compound was estimated by measurements at several concentrations and then estimating the median effective concentration ($EC_{50}$) for causing relaxation. Results are indicated in Table 2. The $EC_{50}$ values in the table are mean estimates obtainer from a minimum of two separate experiments.

TABLE 2

| COMPOUND | $EC_{50}$ ($\mu M$) |
| --- | --- |
| EXAMPLE 3 | 22 |
| EXAMPLE 6 | 0.3 |
| EXAMPLE 7 | 120 |
| EXAMPLE 8 | 120 |
| EXAMPLE 10 | 60 |
| EXAMPLE 11 | 100 |
| EXAMPLE 12 | 20 |
| EXAMPLE 13 | 20 |
| EXAMPLE 14 | 25 |
| EXAMPLE 18 | 50 |
| EXAMPLE 19 | 62 |
| EXAMPLE 26 | 60 |
| EXAMPLE 27 | 30 |
| EXAMPLE 37 | 40 |
| EXAMPLE 38 | 40 |
| EXAMPLE 39 | 40 |
| EXAMPLE 40 | 68 |
| EXAMPLE 42 | 32 |
| EXAMPLE 43 | 40 |

EXAMPLE 46

FROG SKELETAL MUSCLE CONTRACTURE

Rectus abdominis muscles were mounted in 10 ml tissue baths containing frog saline bubbled with oxygen. A resting tension of about 1 g was used. The peak contructure tension in response to a test compound was measured isometrially over a 5 min period. The contractile response was calculated as a percent of the maximal contracture, elicited by a high potassium saline at the beginning and end of the experiment. The median effective concentration ($EC_{50}$) was determined to be the concentration needed to contract the muscle to 50% of its maximal contractile force, as measured with high potassium saline exposure. In many cases, the compounds never produced contractures equivalent to 50% of the high potassium saline-induced contracture force; a minimum $EC_{50}$ was then estimated to be four times the concentration producing a 0–20% contracture. These estimates were mean values obtained from at least two separate experiments.

TABLE 3

| COMPOUND | $EC_{50}$ ($\mu M$) |
| --- | --- |
| EXAMPLE 3 | 16 |
| EXAMPLE 4 | 83 |
| EXAMPLE 6 | 0.42 |
| EXAMPLE 7 | 77 |
| EXAMPLE 8 | >200 |
| EXAMPLE 9 | >200 |
| EXAMPLE 10 | >200 |
| EXAMPLE 11 | >200 |
| EXAMPLE 12 | >200 |
| EXAMPLE 13 | >400 |
| EXAMPLE 14 | >200 |
| EXAMPLE 18 | >200 |
| EXAMPLE 19 | >1000 |
| EXAMPLE 20 | >200 |
| EXAMPLE 22 | >200 |
| EXAMPLE 23 | >520 |
| EXAMPLE 24 | >200 |
| EXAMPLE 25 | >200 |
| EXAMPLE 26 | >200 |
| EXAMPLE 27 | >200 |
| EXAMPLE 37 | >1000 |
| EXAMPLE 38 | >1000 |
| EXAMPLE 39 | >1000 |
| EXAMPLE 40 | >1000 |
| EXAMPLE 42 | >1000 |
| EXAMPLE 43 | >200 |

EXAMPLE 47

PASSIVE AVOIDANCE BEHAVIOR

Male Sprague Dawley albino rats (350–370 g) were injected intraperitoneally with 1 mg/kg of test compounds (in saline solution). Five minutes later, animals were placed in the lighted chamber of the passive avoidance shuttle box. Five minutes later, the door between this chamber and a dark chamber was opened, and the time required for the animal to enter the dark chamber measured. If a particular animal required more than 5 minutes to enter the dark chamber, it was not considered trained and was not used further. As soon as an animal entered the dark chamber, it received a mild shock (0.5 mAmp), and then was removed to the home cage. Ninety-six hours later, the animal was injected with the same test compound, and 5 minutes later placed in the lighted chamber. Five minutes later, the interchamber door was opened and the time required to enter the second, dark chamber again measured. This latter time is termed "latency." Longer latencies mean improved passive avoidance behavior. When some representative compounds of this invention were tested, the drug-tested group showed significant improvement in memory as compared to those animals receiving only saline solution.

Results are shown in Table 4.

TABLE 4

| COMPOUND | UNIT |
| --- | --- |
| EXAMPLE 3 | >0.5 |
| EXAMPLE 6 | 0.43 |

EXAMPLE 48

BILATERAL LESION STUDIES

Passive avoidance testing was conducted in a group of bilaterally lesioned nucleus basalis rats (Sprague Dawley albino, male, 300–500 g) substantially according to the experimental protocol described in Example 47. Anesthetized rats received bilateral infusions of ibotenic acid (5 µg in 1 µl) or phosphate buffer saline in their nucleus basalis regions and were not otherwise treated unless specified until their sacrifice. Animals received their lesions 3 months prior to the beginning of testing. The animals are injected intraperitoneally with 0.5 mg or 2.0 mg/kg of test compounds (in saline solution) 10 minutes before testing. Results are shown in Table 5 and FIGS. 1–2.

Figure 1:
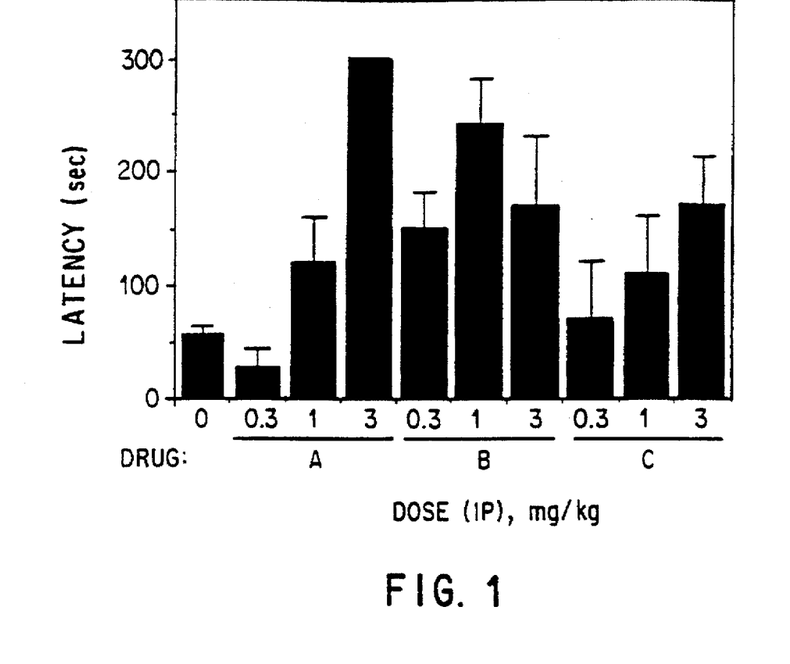
FIG. 1 Passive avoidance behavior following drug injections, wherein compound A represents 3-[(2,4-dihydroxyl)benzylidene] anabaseine, compound B, 3-[(2-hydroxy-4-methoxy)benzylidene] anabaseine, compound C, 5'-methylanabaseine, respectively.

For the results in FIG. 1, 0.3 mg, 1 mg, and 3 mg/kg of test compounds (in saline solution) (Examples 29, 28, 5) were injected to the animals 5 minutes before testing and training. A group of three animals were used for each run and twenty-eight animals were used for control, with $P<0.05$ compared to control (saline), using one way ANOVA.

Figure 2:
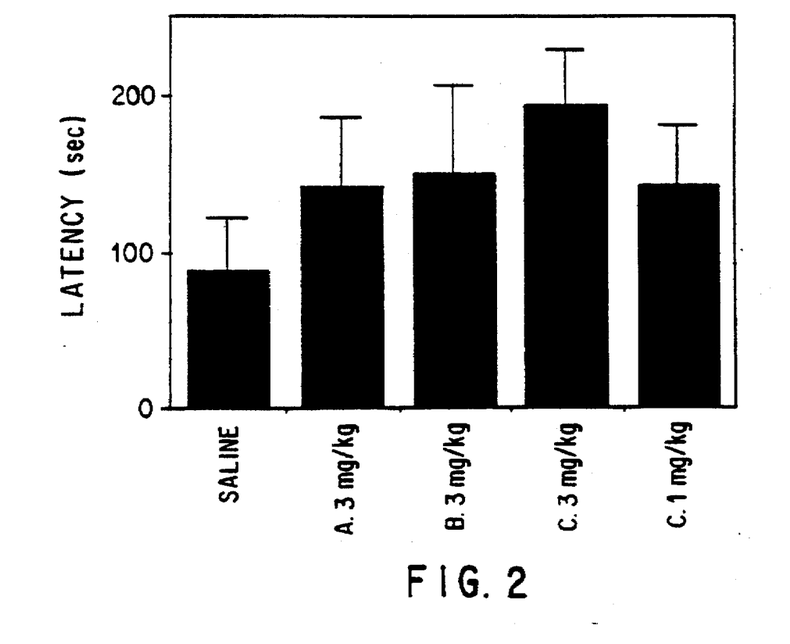
FIG. 2 Passive avoidance behavior following drug injections, wherein compound A represents 3-[(2,4-dipropoxy)benzylidene] anabaseine, compound B, 3-[(2,4-dipentoxy)benzylidene] anabaseine, compound C, 3-[(2,4-dimethoxy)benzylidene]-2-phenyl-3,4,5,6-tetrahydropyridine, respectively.

For the results in FIG. 2, 3 mg/kg of test compounds (in saline solution) (Examples 32, 35, 15) were injected to the animals. A group of three of four animals were used for each run and sixteen animals were used for control, with $P<0.05$ compared to control (saline), using one way ANOVA.

TABLE 5

| COMPOUND | UNIT |
|---|---|
| EXAMPLE 9 | 0.4–0.7 |
| EXAMPLE 12 | 0.1–0.5 |
| EXAMPLE 13 | >0.4 |
| EXAMPLE 14 | 0.4–0.6 |
| EXAMPLE 19 | 0.2–0.3 |
| EXAMPLE 21 | 0.2–0.3 |
| EXAMPLE 22 | >0.5 |
| EXAMPLE 24 | >0.5 |
| EXAMPLE 25 | >0.5 |
| EXAMPLE 37 | 0.2–0.3 |
| EXAMPLE 43 | 0.4–0.6 |

The test results indicate that the tested compounds significantly improved passive avoidance behavior in bilaterally nucleus basalis lesioned rats.

EXAMPLE 49

ACTIVE AVOIDANCE STUDIES

Active avoidance behavior was measured in a group of bilaterally lesioned nucleus basalic rats (Sprague Dawley albino, male, 300–450 g). Animals received their lesions 3 months prior to the beginning of testing. Animals were injected intraperitoneally with 0.05 mg/kg, 0.2 mg/kg, 0.5 mg/kg, 1 mg/kg of the test compound in saline solution (GTS: 3-[(2,4-dimethoxy)benzylidene]anabaseine dihydrochloride; Example 12), and 2 mg/kg of THA (1,2,3,4-tetrahydro-9-aminoacridine), respectively. Ten minutes later, the animals were placed in one chamber of a 2-way active avoidance shuttle. They then received combined cues (sound and light) for 5 seconds; 7 seconds later, they received a mild shock if they did not cross over to the other chamber. If they crossed over before the shock, they received no chock, and this was recorded by the computer as an "avoidance", a sign of potential learning.

Animals received 15 trials/day, every day. Groups of two days were combined, averaged and their SEM calculated.

Figure 3:
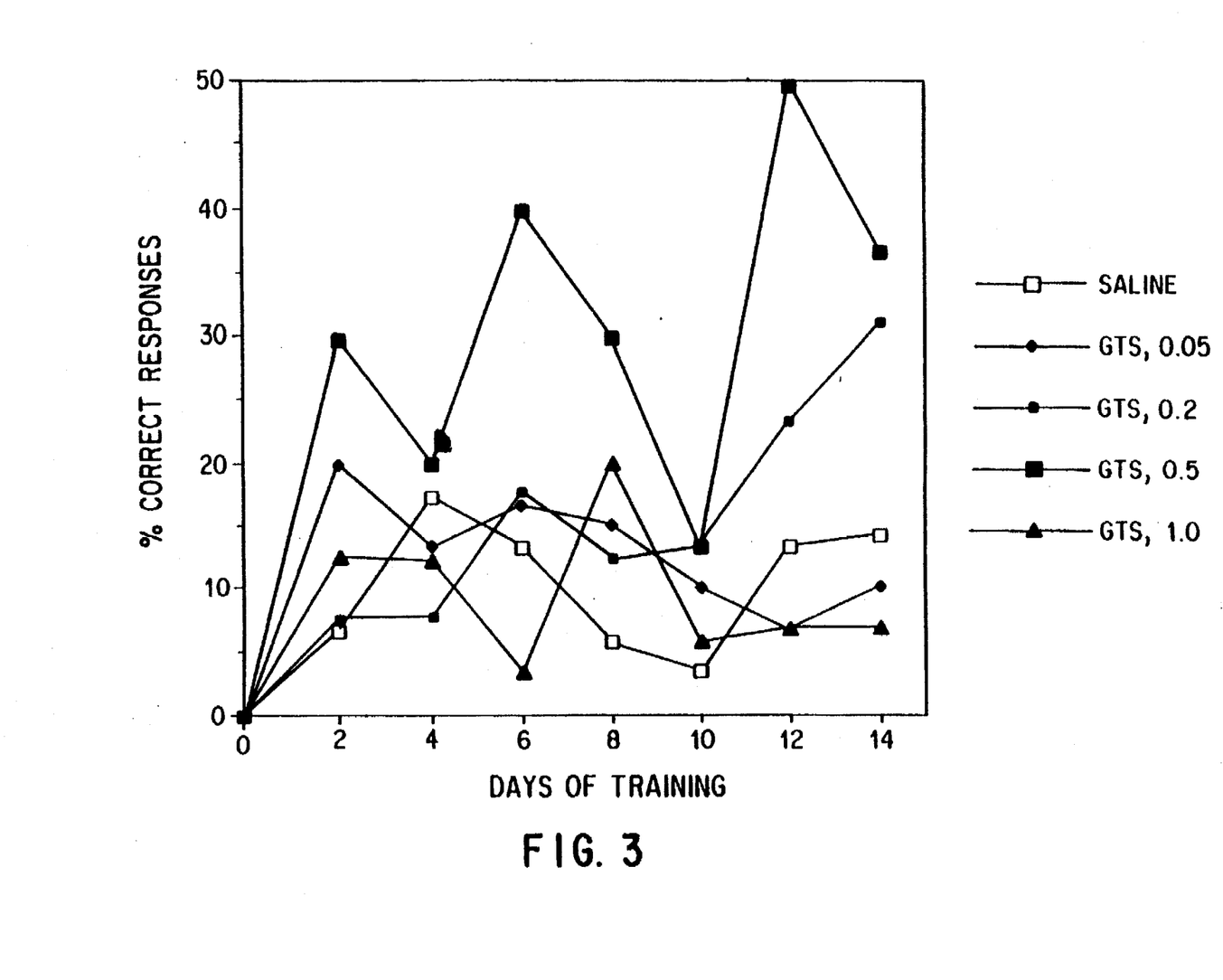
FIG. 3 Effect of GTS on active avoidance behavior at different doses.
Figure 4:
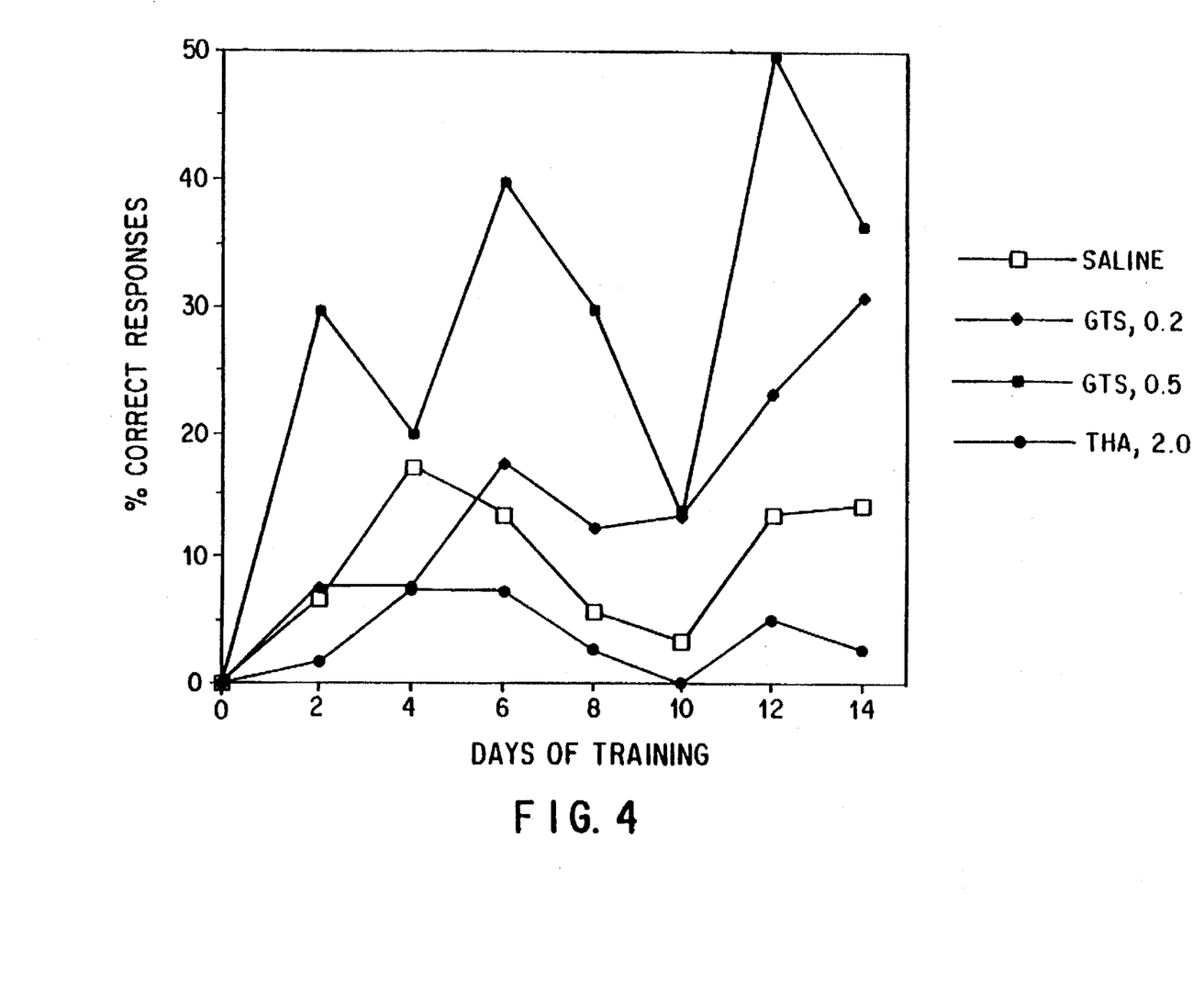
FIG. 4 Effect of GTS and THA on active avoidance behavior.

Test results are shown in FIGS. 3–4.

The results clearly indicate that the test compound significantly enhance the performance of the lesioned animals at the doses of 0.2 and 0.5 mg/kg compared to saline and the 2.0 mg/kg dose of THA.

PREPARATION 1

2-Phenyl-3,4,5,6-tetrahydropyridine

The title compound was prepared substantially according to the procedure of Hu, et al. (J. Labelled Compounds, 10:79, 1974), employing methylbenzoate.

$^1$H-NMR (CD Cl$_2$/TMS): δ1.75 and 1.62 (m, H4 and H5), 2.56 (m, H3), 3.75 (t, J=5.4 Hz, H6), 7.60 (m, phenyl protons), 7.68 (d, phenyl, ortho). MX (FAB) (M+H)$^+$ 160. The title compound is reported in H. Mohrie, et al., (Z. Naturforsch, 41b:1323, 1986).

PREPARATION 2

3-(Benzylidene)anabaseine Dihydrochloride

To a solution of 0.30 g (1.19 mmol) of anabaseine dihydrochloride in 7 ml absolute enthanol was adored 1 ml (9.0 mmol) of benzaldehyde in the presence of catalytic amount (ca. 5 drops) of concentrated HCl. The mixture was kept at 60° C. for 3 days. Then, 40 ml of ethylacetate was added, and the white precipitate was filtered off and recrystallized from methanol—ether to afford 0.33 g (87% yield) of the title compound, m.p. 196°–200° C. (dec.). $^1$H-NMR in (D$_2$O/TSP): 9.008–9.004 m (2H, H2$^1$, H6$^1$), 8.294 (dd 1H, H4$^1$, J$_1$=6.67 Hz, J$_2$=1.44 Hz), 8.045 (dd 1H, H5$^1$, J$_1$=8.10 Hz, J$_2$32 5.52 Hz), 7.599–7.514 m (5H,φ), 7.374 s (1H, φ-C$\underline{H}$=), 3.964 (tr 2H, H6 J=5.74 Hz), 3.125 (dtr 2H, H4, J$_1$=7.19 Hz, J$_2$1.43 Hz), 2.156 (quintett 2H, H5, J=6.08 Hz). The title compound is reported in M. Kawanishi, et al., (Chem. Abstr., 59:11447h, 1963).

The invention now being fully described, it will be apparent to one of ordinary skill in the art that many changes and modifications can be made without departing from the spirit or scope of the invention.

We claim:

1. A compound of the formula:

or a pharmaceutically acceptable salt thereof;

wherein R$^1$ is hydrogen or C$_1$-C$_4$ alkyl; R$^2$ is =CH—X, wherein X is napthyl optionally substituted by N,N-dialkylamino having 1 to 4 carbons in each of the alkyls, styryl optionally substituted by N,N-dialkylamino having 1 to 4 carbons in each of the alkyls, furyl, furylacrolyl or wherein R$^3$, R$^4$, and R$^5$ are each selected from hydrogen, C$_1$-C$_4$ alkyl, C$_1$-C$_6$ alkoxy optionally substituted by N,N-dialkylamino having 1 to 4 carbons in each of the alkyls, amino, cyano, N,N-dialkylamino having 1 to 4 carbons in each of the alkyls, halo, hydroxyl, and nitro, provided that $R^3$, $R^4$ and $R^5$ are not all hydrogen and when two of $R^3$, $R^4$ and $R^5$ are methyl, chloro or methoxy, they are not para to each other and further provided that when $R^1$ is hydrogen or methyl, $R^2$ is not 1-methyl benzylidene or (4-dimethylamine)benzylidene.

2. The compound according to claim 1 where in X is styryl.

3. The compound according to claim 26 wherein X is

4. The compound according to claim 2, wherein the styryl group is substituted by 4-dimethylamino.

5. The compound according to claim 3, wherein $R^3$, which is attached to the 4-position of the phenyl ring, is selected from the group consisting of amino, hydroxyl, chloro, cyano, diethylamino, methyl, methoxy, and nitro; and $R^4$ and $R^5$ are both hydrogen.

6. The compound according to claim 3, wherein $R^1$ is hydrogen, $R^3$ and $R^4$ are both methoxy, and $R^5$ is hydrogen.

7. The compound according to claim 3, wherein $R^3$ is 2-methoxy, and $R^4$ is 4-methoxy.

8. The compound according to claim 3, wherein $R^1$ is hydrogen $R^3$, $R^4$ and $R^5$ are all methoxy.

9. The compound according to claim 3, wherein $R^3$ is 4-methoxy.

10. The compound according to claim 1, wherein X is furyl or furylacroyl.

11. A compound that is 3-(2,4-dimethoxy) benzylidene anabaseine and pharmaceutically acceptable salts thereof.

12. A pharmaceutical composition for improving memory in an animal in need thereof, which comprises an effective amount of a compound of claim 1 and a pharmaceutically acceptable carrier.

13. A composition of claim 12 wherein the compound is 3-(2,4-dimethoxy) benzylidene anabaseine.

14. A method of improving memory in an animal which has memory loss comprising administering to the animal in need thereof a therapeutically effective amount of a compound of claim 1.

15. The method according to claim 14, wherein the animal is human and the memory loss is Alzheimer's disease or Parkinson's disease.

* * * * *

UNITED STATES PATENT AND TRADEMARK OFFICE
CERTIFICATE OF CORRECTION

PATENT NO.   :   5,741,802

DATED        :   April 21, 1998

INVENTOR(S)  :   William R. Kem, John A. Zoltewicz, Edwin M. Meyer, Katalin Prokai-Tatrai It is certified that error appears in the above-identified patent and that said Letters Patent is hereby corrected as shown below:

Col. 25, line 9, after "according to claim", please delete [26] and substitute therefore --1--.

Signed and Sealed this

Twenty-fifth Day of August, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.    : 5,741,802
DATED         : April 21, 1998
INVENTOR(S)   : Kem, et al It is certified that error appears in the above-identified patent and that said Letters Patent is hereby corrected as shown below:

On the title page, item [73], please delete "University of Florida" and substitute therefore -- University of Florida Research Foundation, Inc. --

Signed and Sealed this

Seventeenth Day of November, 1998

Attest:

BRUCE LEHMAN

Attesting Officer       Commissioner of Patents and Trademarks